(12) United States Patent
Buessing

(10) Patent No.: US 8,942,826 B2
(45) Date of Patent: Jan. 27, 2015

(54) IMPLANTABLE DEVICE WITH EXTENDED ELECTRICAL CONDUCTOR

(75) Inventor: Heinrich Buessing, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 663 days.

(21) Appl. No.: 13/301,675

(22) Filed: Nov. 21, 2011

(65) Prior Publication Data

US 2012/0157812 A1   Jun. 21, 2012

Related U.S. Application Data

(60) Provisional application No. 61/424,075, filed on Dec. 17, 2010.

(51) Int. Cl.
*A61N 1/37* (2006.01)
*A61N 1/05* (2006.01)
*A61N 1/08* (2006.01)
*A61B 18/14* (2006.01)

(52) U.S. Cl.
CPC .. *A61N 1/05* (2013.01); *A61N 1/08* (2013.01); *A61N 1/056* (2013.01); *A61B 18/1492* (2013.01); *A61N 2001/086* (2013.01)
USPC ............................. 607/119; 607/122; 600/374

(58) Field of Classification Search
CPC ... A61N 1/056; A61N 1/08; A61N 2001/086; A61B 18/1492
USPC .................................. 600/374; 607/119, 122
See application file for complete search history.

(56) References Cited

U.S. PATENT DOCUMENTS

| 2004/0199071 A1* | 10/2004 | Lardo et al. ................... 600/423 |
| 2009/0171421 A1* | 7/2009 | Atalar et al. ..................... 607/63 |
| 2012/0277840 A1 | 11/2012 | Flach et al. |

FOREIGN PATENT DOCUMENTS

| WO | 2007/047966 A2 | 4/2007 |
| WO | 2010/044019 A1 | 4/2010 |
| WO | 2010/065049 A1 | 6/2010 |

OTHER PUBLICATIONS

Bonmassar, G. "Resistive Tapered Stripline (RTS) in Electroencephalogram Recordings During MRI" IEEE Transactions on Microwave Theory and Techniques, Bd. 52, Nr. 8, Aug. 1, 2004, pp. 1992-1998.
European Search Report dated Jun. 4, 2012, 7 pages.

* cited by examiner

*Primary Examiner* — Tammie K Heller
(74) *Attorney, Agent, or Firm* — ARC IP Law, PC; Joseph J. Mayo

(57) ABSTRACT

Implantable medical device with at least one long extended electrical conductor that is insulated from the surrounding material by a dielectric. The implantable medical device includes an electrode pole that emits therapy signals or detects diagnostic signals, at least one first longitudinal section of a first characteristic impedance between a proximal end and the electrode pole; and at least one second longitudinal section adjacent to the at least one first longitudinal section. The at least one second longitudinal section includes a second characteristic impedance and is shorter than the first longitudinal section. The second characteristic impedance is either larger or smaller than a load characteristic impedance.

19 Claims, 10 Drawing Sheets

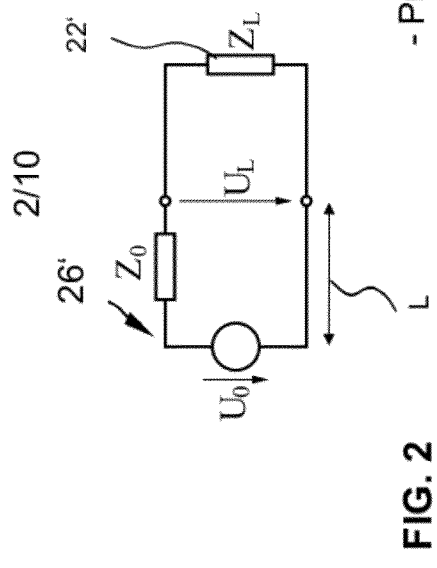
FIG. 2 - Prior Art -
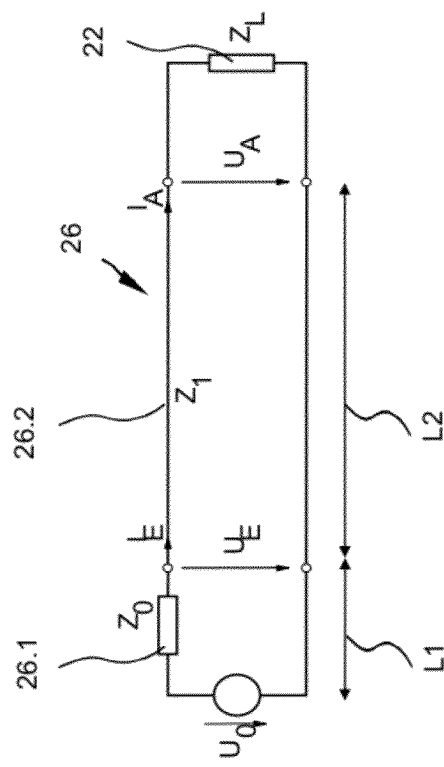
FIG. 3

IMPLANTABLE DEVICE WITH EXTENDED ELECTRICAL CONDUCTOR

This application claims the benefit of U.S. Provisional Patent Application 61/424,075 filed on 17 Dec. 2010, the specification of which is hereby incorporated herein by reference.

BACKGROUND OF THE INVENTION

1. Field of the Invention

At least one embodiment of the invention relates to a permanent or temporary implantable device having a long extended electric conductor.

2. Description of the Related Art

Such devices, for example electrode leads for electrical stimulation, have the disadvantage that the electrical leads thereof can heat up in an MRI machine because the alternating magnetic fields in an MRI machine induce electrical currents in the electrical conductor, which are not insignificant. For this reason, typically patients with heart pacemakers cannot be examined at all in an MRI device nowadays using current technology, or only to a limited degree.

Implantable heart pacemakers or defibrillators typically have at least one stimulation electrode lead attached to said pacemaker, and said electrode lead has a standardized electrical connection at its proximal end, said end being provided for connection to the heart pacemaker or defibrillator; and said electrode lead has one or multiple electrode poles on its distal end, said distal end being provided for placement of the same inside the heart. Such an electrode pole emits electrical impulses to the cardiac tissue (myocardium) and senses electrical fields in order to detect, in connection with the so-called sensing action, cardiac activity. Typically, electrode poles are disposed in the shape of a ring around the electrode lead with electrically conducting surfaces or in the form of a point or tip electrode at the distal end of the electrode lead. The electrode poles are connected to contacts of the electrical connection of the electrode lead on the proximal end thereof, in an electrically-conducting manner via one or multiple electrical leads. Thus, between the contacts of the electrical connection of the electrode leads there extend at their proximal ends and between the electrode poles at the distal end of the electrode lead there are one or several electrical leads that electrically connect one or several of the electrode poles with one or several of the contacts. These electrical leads can be used, on the one hand, for the transmission of stimulation impulses to the electrode poles or for the transmission of electrical signals to the proximal end of the electrode line that were recorded by the electrode poles; in the context of the further description below a lead of this type will be referred to as a functional lead. Such functional leads are electrical conductors that are necessary for the functions of the respective electrode lead; as such they are at risk in that external alternating magnetic fields induce currents in them that may, for example, result in an undesired heating of the functional leads or of the electrode poles connected thereto.

BRIEF SUMMARY OF THE INVENTION

The object of at least one embodiment of the invention is to provide a device that will resolve the problem that has been outlined above.

According to at least one embodiment of the invention this object is achieved by providing a temporary or permanent implantable medical device having at least one long extended electrical conductor comprising a functional lead that is insulated from surrounding material by a dielectric having an inside diameter $d_{iel}$ that is connected with an electrode pole for the output of therapy signals or for the detection of diagnostic signals, which represents in its implanted state a load impedance $Z_L$ for electromagnetic waves;

that has between its proximal end and the electrode pole at least one longitudinal section of a first characteristic impedance $Z_0$ for electromagnetic radio frequency waves; and that has immediately adjacent to the first longitudinal section a second longitudinal section, at least 0.25 long inside diameters ($d_{iel}$) long, that is shorter in comparison to the first longitudinal section having a second characteristic impedance $Z_1$ for electromagnetic radio frequency waves, and wherein the second characteristic impedance is greater or smaller than the first characteristic impedance and greater or smaller than the load impedance of the electrode pole.

The electrical conductor of the medical device according to at least one embodiment of the invention comprises a functional lead that has lead sections with preferably strongly varying characteristic impedances between its proximal end and a connected electrode pole. These dampen and transform a transition resistance from the connected electrode pole to the tissue in such a way that a mismatch for high frequency can be achieved, and this results in the implanted state in the fact that, if high frequency magnetic alternating fields act upon them, such as are used for magnetic resonance tomography, the effective power that is transmitted to the tissue is reduced. This allows for a noticeable reduction of the heating of the tissue, in particular in the proximity of the electrode pole or perhaps in the proximity of the electrode poles.

The electrical conductor is preferably an electrode lead for diagnosis or therapy of cardiac activity.

The difference between the first and the second characteristic impedance is manifested in the embodied examples of the medical device in such a way that a real part of the second characteristic impedance for electromagnetic radio frequency waves is smaller by a factor of at least two than a real part of the first characteristic impedance. Preferably, this difference is even greater, with the named factor being at least five, and in especially preferred embodied examples at least ten.

Investigations by the inventors have shown that in comparison with the first longitudinal section the shorter, the second longitudinal section should be at least one quarter of the inside diameter of the dielectric ($d_{iel}$ in FIG. 7) or at least ten dielectric layer thicknesses ($d_2$ in FIG. 7) long in order to reduce the heat transfer.

Up to a length of the second longitudinal section of one quarter of the inside diameter of the lead dielectric the inventors found in experiments with weak damping by the outside conductor (the tissue) an increase of the real power of a point (tip) electrode of an electrode lead that was used in experiments.

The effectiveness of the second longitudinal section for reducing the real power that is transferred to the tissue thus increases with the increasing length of the second longitudinal section. Especially favorable lengths for the second longitudinal section are in the range to a maximum of 5 $d_{iel}$. Preferably, the second longitudinal section will not exceed a length of approximately 10 $d_{iel}$. The effectiveness of the second longitudinal section depends also on the degree of damping that radio frequency waves are subjected to in the transmission line. The greater the damping is, the lower the real power at the electrode pole.

The functional lead with its different longitudinal sections can be realized in different ways. In some embodied examples the functional lead has a center conductor and a hollow-cylindrical outside conductor, and wherein the center conductor in the second longitudinal section has a geometric shape that deviates from that of the center conductor in the first longitudinal section. For example, the center conductor has the shape of a hollow coil in the first longitudinal section and the shape of a cylinder in the second longitudinal section. The cylinder-shaped second longitudinal section of the center conductor has in this type of implementation in one variant a larger diameter than the hollow-coil of the center conductor in the first longitudinal section. But it should be separated from the outside conductor by an inside dielectric; i.e., it should be electrically insulated. This inside dielectric can be realized as a coating or a film. The prior art provides possible layer strengths of a little as ca. 100 nm or even less; e.g. via PVD (plasma vapor deposition) or CVD (chemical vapor deposition). The thinner the layer thickness, the stronger is the reduction of the power that is transmitted to the tissue. But very thin layers are more susceptible to mechanical stresses. Due to scouring or scratches, they may, for example, lose their electric insulating properties.

A preferred compromise solution between electric effectiveness and mechanical stability is a layer thickness of 0.5 μm to 2.5 Mm; especially preferred is 1 μm.

In the alternative, the center conductor can be configured as a feed cable and as a hollow-coil shape in the second section.

At least one embodiment of the invention is applied in electrode leads having any type of electrode poles. The electrode pole can, for example, be configured as a tip electrode pole or as a ring electrode pole. It is also possible to envision several electrode poles on one functional lead. In some embodied examples the electrode pole follows directly after the second longitudinal section of the functional lead. In terms of manufacture this is advantageous because the first longitudinal section does not need to be interrupted. But in one variant the second longitudinal section may be embedded at a distance from the electrode pole in the functional lead, resulting in the second longitudinal section to be surrounded in both longitudinal directions by lead sections of the type of the first longitudinal section.

In addition to the embodiments described herein other alternative embodiments may include some or all of the disclosed features.

Subsequently, the medical device according to at least one embodiment of the invention will be explained in further detail in reference to the figures.

BRIEF DESCRIPTION OF THE DRAWINGS

Shown are in:

FIG. 2 an equivalent electrical circuit of a functional lead that is connected to an electrode pole according to the prior art;

FIG. 3 an equivalent electrical circuit of a functional lead that is connected to an electrode pole according to one embodied example of at least one embodiment of the invention;

DETAILED DESCRIPTION OF THE INVENTION

Figure 1:
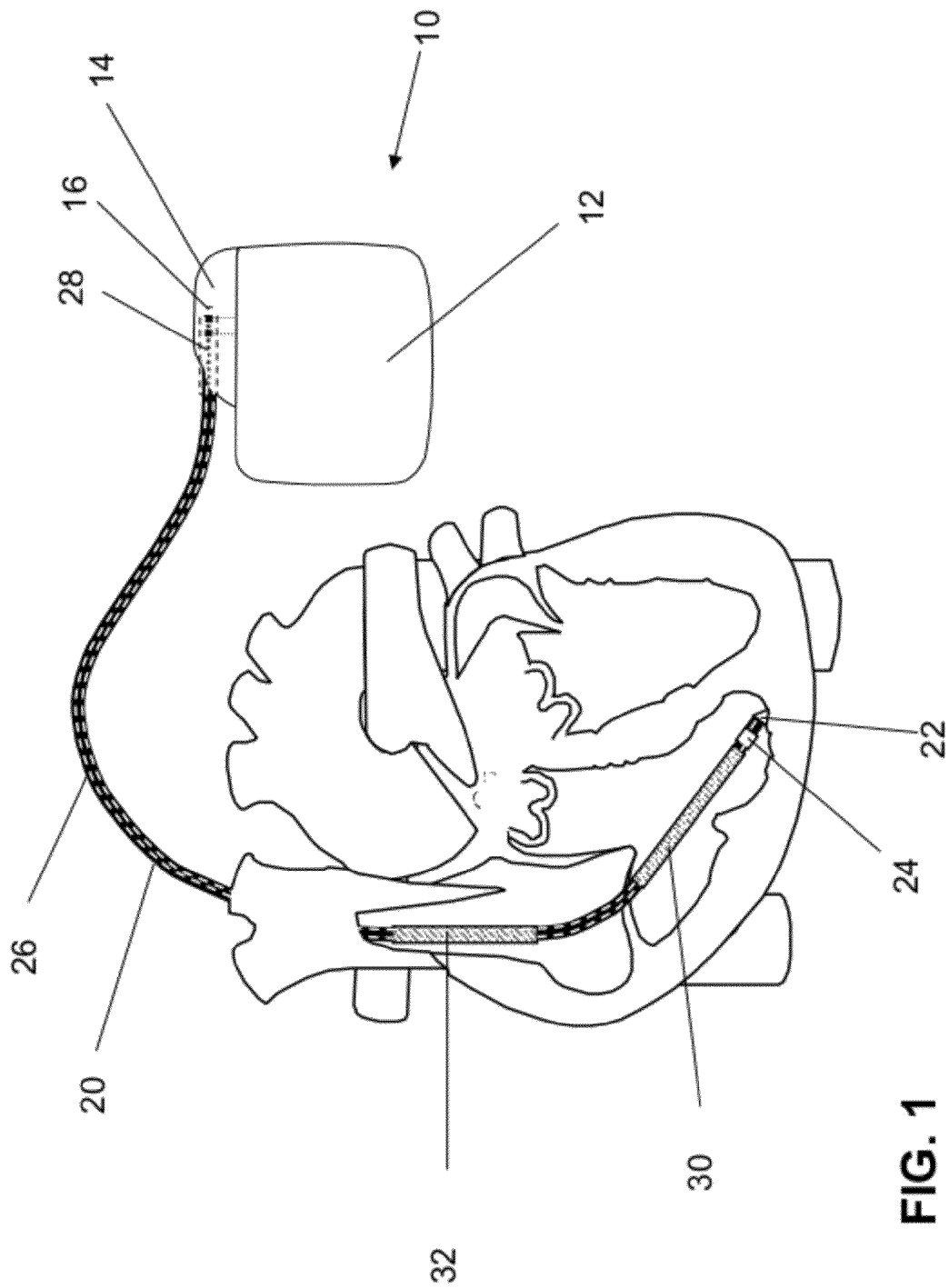
FIG. 1 embodied examples of medical devices in the form of a cardiac pacemaker and an electrode lead connected thereto.

As an example of implantable medical devices, FIG. 1 shows an implantable heart stimulator 10 and an implantable electrode lead 20 connected to the same.

The implantable heart stimulator 10 can be a heart pacemaker or a cardioverter/defibrillator (ICD). In the illustrated embodiment the heart stimulator 10 is a ventricular heart pacemaker and defibrillator. Other known heart stimulators are two-chamber heart pacemakers designed to stimulate the right atrium and the right ventricle, or biventricular heart pacemakers which can stimulate the left ventricle in addition to the right ventricle.

Such stimulators typically have a housing 12, which usually is made of metal, and is consequently electrically conducting and can serve as a large-surface area electrode pole. Typically, a connection housing 14 is attached to the outer side of the housing, which is also referred to as a header. Such a header typically comprises contact connectors serving as receptacles for plug contacts. The contact connectors have electrical contacts 16 that are connected via the appropriate leads to the electronics arranged inside the housing 12 of the heart stimulator 10.

Within the meaning of at least one embodiment of the invention, the electrode lead 20 also constitutes an implantable medical device. Electrode poles, in the form of a point or tip electrode 22 as well as one ring electrode 24 arranged near said electrode poles, are arranged at the distal end of the electrode lead 20 in a conventional manner. The electrode poles 22 and 24 are configured in such a manner that they, depending on the function of the cardiac stimulator to which the electrode line 20 is connected, serve to sense electrical potentials of the (myocardial) heart tissue, or they serve to discharge electrical signals, for instance to release stimulation impulses to the heart tissue surrounding the electrodes. FIG. 1 shows how the electrode poles, that is, the tip electrode 22 and the ring electrode 24, and in certain cases electrode lead 20 are located inside the apex of a right ventricle of a heart.

Both the tip electrode 22 and the ring electrode 24 are electrically connected to a plug contact 28 at the proximal end of the electrode lead 20 via at least one electrical conductor 26 each. The plug contact 28 has electrical contacts that correspond to the electrical contacts 16 of the contact connector in the connection housing 14 of the implantable heart stimulator.

As described in greater detail below, the electrical conductors 26 in the electrode lead 20 can be constructed in different longitudinal sections as primarily extended feed cables or as helix-shaped coiled leads. Such leads, which connect the functional electrode poles with electrical contacts of the plug contact on the proximal end of the electrode lead 20 in an electrically conducting manner, are also characterized in the scope of this description as functional leads because they transmit therapeutic electric signals from the plug contact to the respective electrode poles, or they convey sensed electrical potentials to the plug contact, said potentials representing signals from the respective electrode poles. Consequently, said leads serve to fulfill the elementary function of the medical device.

The electrical functional leads 26 that connect the electrode poles 22 and/or 24 with the electrical contacts of the plug 28 of the electrode lead 20 are jacketed by an insulating coat over the largest part of their length so that any electrical contact to the cardiac tissues occurs in a targeted manner via the electrode poles.

In addition to the electrode poles 22 and 24, which typically serve to stimulate the heart tissue (in this case, ventricular tissue), the electrode lead 20 has two additional even larger-surface area electrode poles 30 and 32, which function as defibrillation electrodes and are constituted by at least one un-insulated helix-shaped coiled wire.

It is to be noted that at least one embodiment of the invention is explained in the present context of this embodied example using of a right ventricular heart pacemaker and defibrillator. However, in principle, an ablation electrode lead could also be adduced as an example of a medical device in the sense of at least one embodiment of the invention, wherein the ablation electrode lead likewise projecting into the heart of a patient and being controlled by a device outside the patient's body and, for that purpose, connected to the same. Furthermore, such electrode leads can also function in other applications, upon technical adjustment for the special requirements of other specific uses, to stimulate tissue or relay signals to/from nerves, the brain, and other organs, or as feeds from implantable sensors.

FIG. 2 shows an equivalent electrical circuit of a functional lead of an electrode conductor according to the prior art.

The functional lead 26' constitutes in its longitudinal extension L a first characteristic impedance $Z_0$. The electrode pole 22' constitutes a load characteristic impedance $Z_L$. At the proximal end of the functional lead, which will subsequently also be referred to as the start of the functional lead, there is applied a voltage $U_0$. Via an electrode pole 22' at the distal end of the functional lead a voltage $U_L$ decreases.

The electrode pole 22' that is constituted by the electrode tip, as is explained further below in reference to FIGS. 4 to 6, can be represented, for example, by a complex load characteristic impedance of $$Z_L = 233 - j138 \Omega$$

against the body tissue.

But if the functional lead, contrary to FIG. 2, contains over its longitudinal extension a first longitudinal section L1 and a second longitudinal section L2 that differs from the first, specifically in the form of a conductor lead piece of the length l with a second characteristic impedance $Z_1$ that differs from the first characteristic impedance $Z_0$ and from the load characteristic impedance $Z_L$, which transforms the load characteristic impedance $Z_L$ to $\tilde{Z}_L$, the situation is quite different. The equivalent electrical circuit of such a functional lead 26 according to at least one embodiment of the invention is depicted in FIG. 3.

The functional lead 26 now has the two longitudinal sections L1 and L2. Their length ratio relative to each other as shown in FIG. 3 is not depicted in correspondence with the actual ratio. In fact, the first longitudinal section L1 with a functional lead piece 26.1 is considerably longer than the second longitudinal section L2 with a functional lead piece 26.2. The second longitudinal section L2 has a length l and characteristic impedance $Z_1$.

Toward the proximal end of the functional lead 26, at the start of the second longitudinal section, there is a voltage $U_E$ applied; and at the distal end of the of the functional lead 26, which is in the present example at the same time the end of the second longitudinal section L2, there is applied voltage $U_A$ relative to load characteristic impedance of the electrode pole 22.

The voltages and currents $U_E$, $I_E$, $U_A$ and $I_A$ at the start and at the end of the second longitudinal section L2 can be divided in an out-going wave and a returning wave:

$$U_E = U_H e^{jkl} + U_R e^{-jkl} \tag{1.a}$$

$$I_E = \frac{1}{Z_1}(U_H e^{jkl} - U_R e^{-jkl}) \tag{1.b}$$

$$U_A = U_H + U_R \tag{1.c}$$

$$I_A = \frac{1}{Z_1}(U_H - U_R) \tag{1.d}$$

The load characteristic impedance $Z_L$ and transformed load characteristic impedance $\tilde{Z}_L$ are calculated based on the out-going and returning waves as follows:

$$Z_L = Z_1 \frac{U_H + U_R}{U_H - U_R} \tag{2.a}$$

$$\tilde{Z}_L = Z_1 \frac{U_H e^{jkl} + U_R e^{-jkl}}{U_H e^{jkl} - U_R e^{-jkl}} \tag{2.b}$$

A conversion for the transformed load characteristic impedance results in $$\tilde{Z}_L = \frac{Z_L \cos(kl) + jZ_1 \sin(kl)}{jZ_L \sin(kl) + Z_1 \cos(kl)} \tag{3}$$

The power is calculated with $$P = U \cdot I^* \tag{4}$$

Orders of magnitude symbols having superscripted asterisks designate the complex conjugate of a respective number.

Thus, the power that flows into the second longitudinal section can be calculated as follows:

$$P_E = U_E \cdot I_E^* = U_0 \frac{\tilde{Z}_L}{\tilde{Z}_L + Z_0} \cdot U_0^* \frac{1}{(\tilde{Z}_L + Z_0)^*} \tag{5}$$

$$P_E = U_E \cdot I_E^* = |U_0|^2 \frac{\tilde{Z}_L}{|\tilde{Z}_L + Z_0|^2} \tag{6}$$

The power at the load characteristic impedance, which means in the tip of the electrode, can be calculated based on the out-going and returning wave.

$$P_L = (U_H + U_R) \cdot \frac{(U_H + U_R)^*}{Z_L^*} = \frac{|U_H + U_R|^2}{Z_L^*} \quad (7)$$

Derived with $$U_E = \tilde{Z}_L I_E \quad (8)$$

from equation (1.b) is $$\frac{Z_1}{\tilde{Z}_L} U_E = Z_1 I_E = U_H e^{jkl} - U_R e^{-jkl} \quad (9)$$

thus resulting, by inserting and converting equations (1.a) and (1.b), in $$U_H = \frac{1}{2}\left(1 + \frac{\tilde{Z}_L}{Z_1}\right) U_E e^{-jkl} \quad (10a)$$

$$U_R = \frac{1}{2}\left(1 - \frac{\tilde{Z}_L}{Z_1}\right) U_E e^{jkl} \quad (10b)$$

$$P_L = \frac{1}{Z_L^*}\left|\left(1 + \frac{\tilde{Z}_L}{Z_1}\right) \cdot e^{-jkl} + \left(1 - \frac{\tilde{Z}_L}{Z_1}\right) \cdot e^{jkl}\right| \cdot \frac{1}{4} U_E^2 = \frac{U_E^2}{Z_L^*}\left|\cos(jkl) - j\frac{\tilde{Z}_L}{Z_1}\sin(jkl)\right| \quad (11)$$

Figure 5:
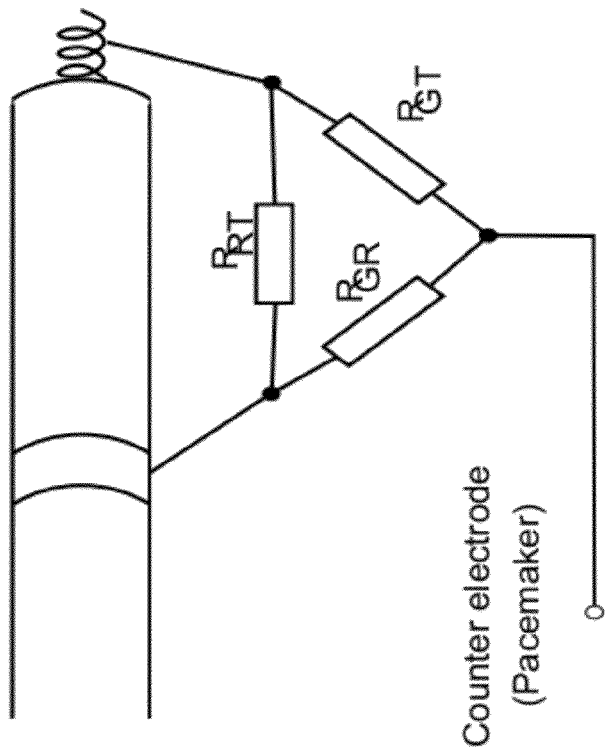
FIG. 5 in a schematic equivalent electrical circuit, equivalent resistances between the electrode poles tip and ring of an electrode lead and its auxiliary electrode in a delta configuration.
Figure 4:
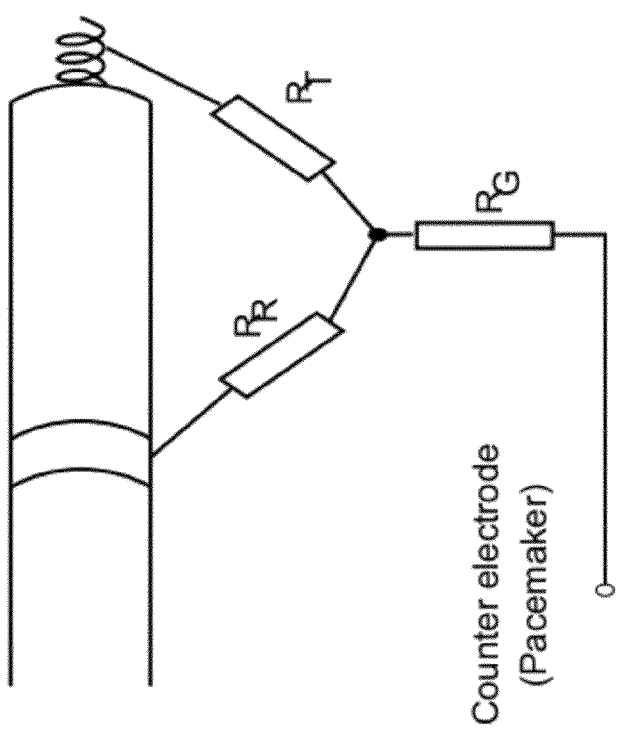
FIG. 4 in a schematic equivalent electrical circuit, equivalent resistances between the electrode poles tip and ring of an electrode lead and its counter electrode in a Y-configuration.
Figure 6:
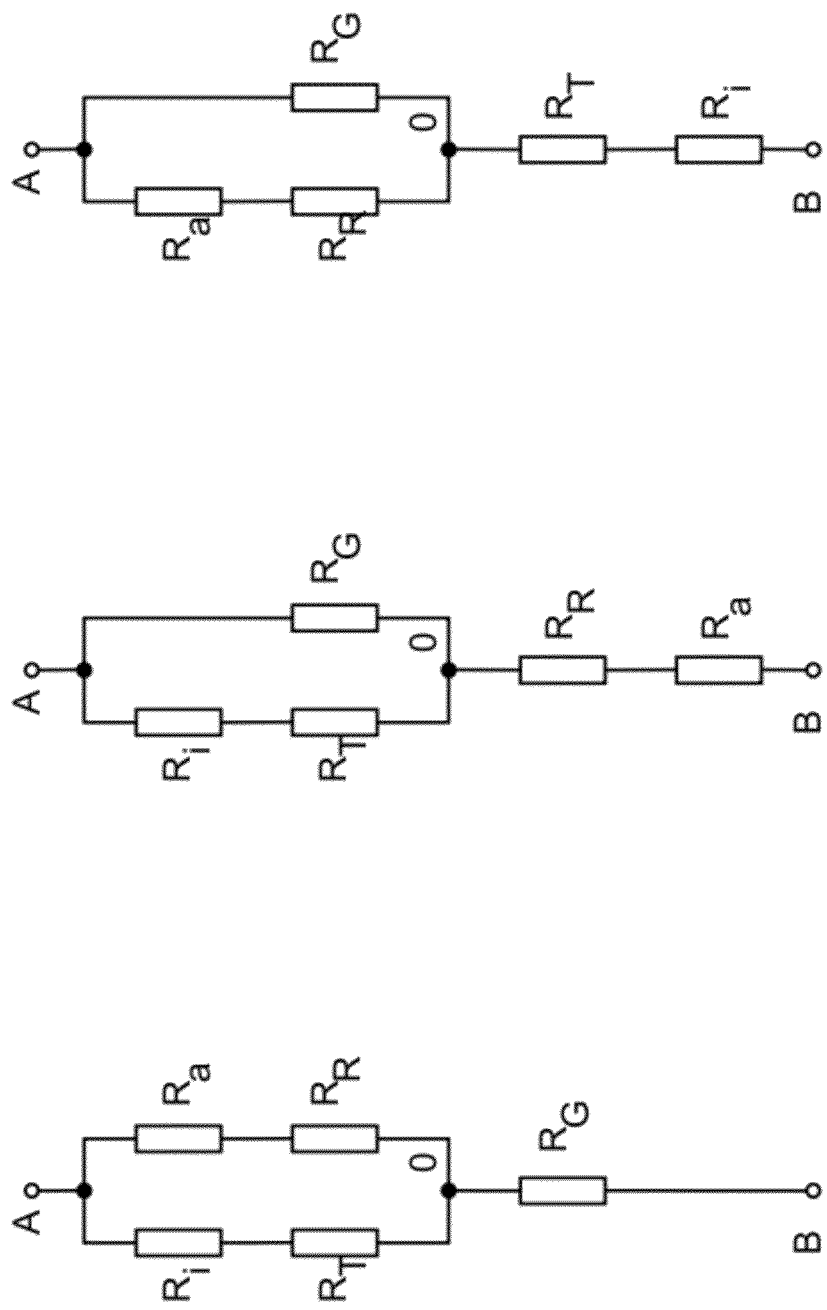
FIG. 6 three constellations in which, respectively, one total resistance is measured between two points A and B in order to calculate partial resistances RT, RR and RG of the equivalent electrical circuits from FIGS. 4 and 5 for different frequencies.

Now follows, based on FIGS. 4, 5 and 6, an explanation regarding the determination of the frequency-dependent characteristic impedance values that are to be used as a basis.

FIGS. 4 and 5 show in a schematic equivalent electric circuit equivalent resistances between the electrode poles point (tip) 22 and ring 24 of an electrode lead 22 and its counter electrode in a Y-configuration (FIG. 4) and a delta configuration (FIG. 5).

FIG. 6 shows those three constellations in which a total resistance is measured respectively between two points A and B. Based on the total resistances of these three networks, it is possible to calculate for each frequency that is used as a measuring frequency the partial resistances RT, RR and RG, respectively.

Taken into account for the calculation of the resistances of the electrode poles are a resistance of the interior coils Ri, which is measured at 37.6Ω, and a resistance of the outside coils Ra, which is measured at 106.7Ω for each of the used frequencies. The line resistance of the counter electrode is assessed at 0Ω. Ri and Ra are separately measured and known.

Two different electrode leads were measured that were held inside a glass filled with a physiological saline solution, with a counter electrode made of platinum-iridium alloy. In order to first isolate inductivity, capacity and resistance of the lines, and using different frequencies and an LCR meter, type: Fluke PM6306, the impedance between the center and outside conductors of an electrode lead with its tip either in solution or freely suspended in air were measured.

The measured results that the inventors established in the context of an experimental series are compiled below in Table 1. Each line of the table features two values that are listed one above the other and that were measured using two different electrode leads.

TABLE 1

| Frequency | Tip vs. ring with head in solution | | Tip vs. ring with head in air | |
|---|---|---|---|---|
| | R/Ω | C/nF | R/Ω | C/nF |
| 1 MHz | 275.7 | 64 | 58 | 75.3 |
| | 222.2 | Not measurable | 34.9 | 59.8 |
| 500 kHz | 277.8 | 340 | 55.2 | 83.3 |
| | 222.7 | 0.13 | 38.0 | 68.9 |
| 200 kHz | 278.4 | 514 | 57.06 | 83.23 |
| | 223.8 | 412 | 38.15 | 67.7 |
| 100 kHz | 278.87 | 721.4 | 56.65 | 83.18 |
| | 224.22 | 523 | 40.15 | 67.68 |
| 50 kHz | 279.74 | 1029 | 66.24 | 83.19 |
| | 225.37 | 641 | 51.70 | 67.73 |
| 20 kHz | 281.3 | 1630 | 115.8 | 83.22 |
| | 227.8 | 890 | Not measurable | 67.74 |

The measured values in this above table indicate that starting with frequencies of greater than 500 kHz the inductivity of the lead plays in fact a role when measuring with open head. Based on measurements with head in the air (interruption between center and outside conductor and/or between tip and ring) it was possible to determine the value of the capacitance per unit length between inside and outside coil as 140 to 150 pF/m.

The unit-length resistance of inside and outside coils can be determined with head under water at frequencies of below 500 kHz by subtracting the resistance between tip and ring. When measuring with head in saline solution it can be seen that at a higher frequency the inductivity of the lead increasingly influences the measured result and, depending on the electrode type, in the present instance Setrox S40, the capacity of the lead can even equalize already starting at a frequency of 1 MHz.

At lower frequencies of around 20 kHz, shown as capacitive reactance, the Faraday capacity of both electrodes in the table demonstrates strong differences and is much too low. Damage to the fractal structure of tip and ring due to clamping of the electrode tips during previous measurements are believed to be the cause for this. But the measured values after 50 kHz frequency are almost not influenced by this at all.

It was found that the measured resistance values are not influenced by the position of the electrode head relative to the counter electrode if the electrodes are still more than approximately four centimeters apart from each other. This allows for the conclusion that the resistances RT, RR and RG in FIG. 4 are the resistances of the respective electrode pole vs. an infinite remote point with zero potential.

The resistances of the electrodes among each other were measured on the electrode as follows:

TABLE 2

| Frequency | Tip und ring vs. counter electrode | Ring and counter electrode vs. tip | Tip and counter electrode vs. ring |
|---|---|---|---|
| 1 MHz | 77.7Ω | 137.6Ω | 156Ω |
| | 1.64 μH | 70 nF | 3.26 μH |
| 500 kHz | 77.8Ω | 137.8Ω | 155.4Ω |
| | 2.5 μH | 0.22 μH | 3.98 μH |
| 200 kHz | 77.9Ω | 138.04Ω | Not measurable |
| | 3.0 μH | 1.44 μF | |
| 100 kHz | 78.2Ω | 138.48Ω | 154.77Ω |
| | Not measurable | 1.222 μF | 3.41 μH |
| 50 kHz | 78.538Ω | 139.22Ω | 154.86Ω |
| | Not measurable | 1.5 μF | 3.49 μH |
| 20 kHz | 79.026Ω | 140Ω | 155.20Ω |
| | 9.11 μF | 2.3 μF | 28.27 μF |

The following values as compiled in Table 3 result for the resistances of the tip, ring and counter electrodes at different frequencies. The average value (Ø) is printed in bold typeface and entered in the lower line; assumed for RT and RR was the mean value and for RG the median.

TABLE 3

| Frequency | RT | RR | RG |
|---|---|---|---|
| 1 MHz | 91.88Ω | 41.15Ω | 8.70Ω |
| 500 kHz | 91.81Ω | 40.28Ω | 9.01Ω |
| 100 kHz | 91.94Ω | 39.11Ω | 9.63Ω |
| 50 kHz | 92.51Ω | 39.02Ω | 9.83Ω |
| 20 kHz | 92.99Ω | 39.06Ω | 10.17Ω |
| Ø | 92.2Ω | 39.7Ω | 9.6Ω |

The conductivity of the electrolyte is adjusted to $\sigma=1.57 \ldots 1.67$ S/m and its permittivity is $\in=80 \cdot 8.85 \cdot 0.10{-}12$ As/Vm allowing to extrapolate using the formula $$C = \frac{1}{R} \cdot \frac{\varepsilon}{\sigma}$$

and which capacity must be envisioned as parallel relative to the resistances. It is listed in the table together with the capacitive reactance at 64 MHz. The measured values for tip and ring fluctuate around 1.2% (tip) and/or 2.7% (ring); the tolerance for the conductivity of the physiological saline solution fluctuates around 6.2%, which is why upward and downward deviations of 10% must be expected.

TABLE 4

| | Tip | Ring | Counter electrode |
|---|---|---|---|
| | Capacity | | |
| C | 4.54 pF ... 4.95 pF | 10.4 pF ... 11.7 pF | 37.4 pF ... 54.2 pF |
| Ø | 4.74 pF | 11.0 pF | 45.5 pF |
| | Capacitive reactance at 64 MHz | | |
| | (Larmor frequency at MRI in 1.5T equipment) | | |
| XC 64 MHz | $-j503\Omega \ldots -j547\Omega$ | $-j212\Omega \ldots -j238\Omega$ | $-j45\Omega \ldots -j65\Omega$ |
| Ø | $-j524\Omega$ | $-j226\Omega$ | $-j55\Omega$ |
| | Resistance converted to saline solution according to ASTM | | |
| | ($\sigma = 0.474$ S/m) | | |
| R Ø | 315Ω | 136Ω | 33Ω |
| | Resistance converted to a 0.03 molar solution | | |
| | ($\sigma = 0.310 \ldots 0.370$ S/m) | | |
| R Ø | 440Ω | 190Ω | 46Ω |

A saline solution with $\sigma=0.474$ S/m provides the correct results for the measurement of the heating according to the ASTM standard (American Standard for Testing and Material), while a 0.03 molar saline solution delivers the correct values for the resistance of tip and ring for sensing and pacing inside tissue.

Figure 7:
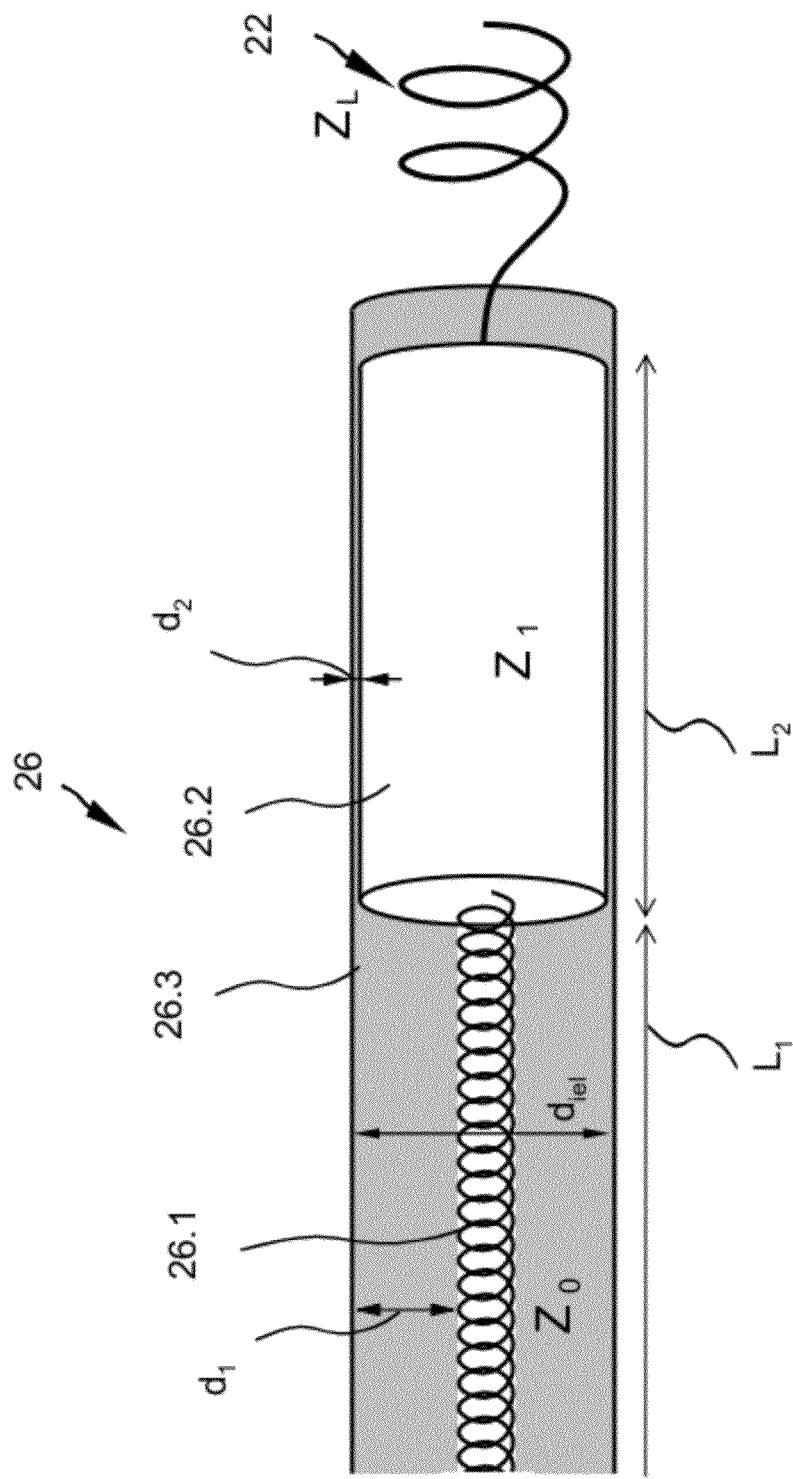
FIG. 7 a schematic depiction of an example of a functional lead of an electrode conductor.

FIG. 7 shows a schematic representation of an example of a functional lead of an electrode conductor. The embodied example can also be represented by the equivalent electrical circuit in FIG. 3. Correspondingly, the reference symbols that have been used in FIG. 7 are for the most part identical with the reference symbols that have been used in FIG. 3. The functional lead 26 comprises a first longitudinal section L1 that is not shown in its full length in which the center conductor is executed as a hollow coil 26.1 and constitutes characteristic impedance $Z_0$. In this first longitudinal section L1, the center conductor 26.1 is surrounded by an insulation 26.3; e.g., a silicone insulation with a relative primitivity of $\in_r=3$ and a fading electrical conductivity $\sigma=0$ S/m.

In the, relative to the first longitudinal section L1, comparatively very short second longitudinal section L2 of the functional lead 26 the center conductor is constituted as a cylindrical conductor 26.2 of, for example, 2 millimeters diameter and 10 millimeters length and jacketed by an insulation layer, an internal dielectric (for example, a paint film) of a strength d2 of 10 micrometers. This cylindrical conductor 26.2 has a characteristic impedance for electromagnetic radio frequency waves of $Z1=(13.16+j6.67)\Omega$.

In comparison: in the first longitudinal section L1 the hollow coil 26.1 has clearly higher characteristic impedance for electromagnetic radio frequency waves, as can be seen in connection with the calculations and measurements as established in the context of FIGS. 4 to 6. The corresponding characteristic impedance of the electrode pole 22 is (at $\in_r=80$, $\sigma=0.47$ S/m for body tissues), as mentioned e.g. $Z_L=233-j138\Omega$, and is therefore clearly above that of the center conductor piece 26.2 in the second longitudinal section L2 as well.

Figure 8:
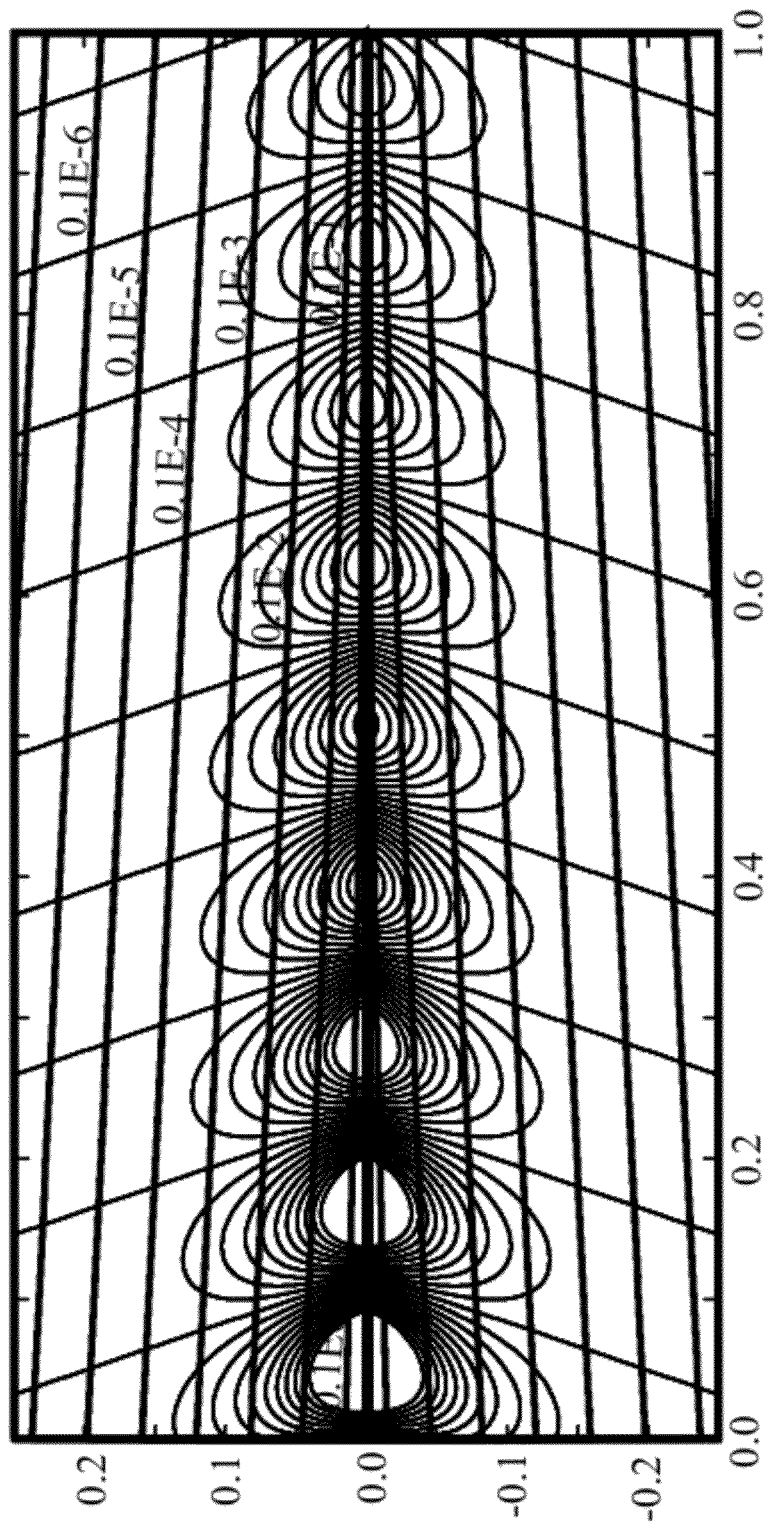
FIGS. 8 and 9 one graphic representation, respectively, of the result of a simulation calculation that reflects electromagnetic energy and magnetic field lines around a longitudinal section of 0 to 1 meter of a long extended electrical conductor according to the prior art and/or according to an embodied example of at least one embodiment of the invention.

FIG. 8 shows a graphic depiction of the results of a simulation calculation that reflects the electrical field strength as well as magnetic field lines and/or contour lines of magnetic flux tubes around a longitudinal section of 0 to 1 meter of a long extended electrical conductor according to the prior art, which corresponds to the equivalent electrical circuit in FIG. 2 and has an inner electrolyte diameter $d_{iel}$ of 2 mm.

The thinly drawn lines are field lines and/or flux tubes. They show the course of the field that forms around the abscissa of the cylindrical lead extending in the diagram when a high-frequency wave propagates in the plane of the drawing from left to right along the lead. On the ordinate the distance from the abscissa is plotted in meters −0.25 and +0.25 meters. Negative distance values are to be understood as distances in the opposite direction of the direction of positive distance values. The lines drawn in bold are isolines and encode the electromagnetic energy that is located in the respective radius elements $2\pi\rho d\rho$.

The electromagnetic energy is to be understood as energy that is averaged over time, which means it is not the largest in places where the field lines are closely spaced next to each other, but generally close relative to the lead.

The energy value drops logarithmically by a factor ten between two isolines. Due to the fact that the field line balls become smaller toward the right, and/or the isolines are tapered toward the right, it becomes clear to the observer that the field gets weaker toward the right, which means the lead is damped.

The figure shoes the field pattern around an electrode according to the prior art in the body tissues having a conductivity of $\sigma=4.74$ S/m and relative permittivity $\in_r=80$ upon which the wave propagates at 64 MHz. The complex-value characteristic impedance in this example is $$Z_0=162.5+j12.34\Omega.$$

The electrode tip can be represented by a complex resistance of $Z_L=233-j138\Omega$ vs. the body tissues. The load impedance differs in its order of magnitude not substantially from the internal resistance so that in this example 61% of the maximally possible real power is implemented.

The magnetic field lines circle in a cylindrically round fashion around the conductor and are exactly perpendicular at every location relative to the electrical field lines. Thus, presently this is the propagation of a transversal electromagnetic (TEM) wave. It can be seen that an insulated wire, like an electrode lead, represents a conductor in body tissue, upon which the TEM wave can propagate. This conductor has a frequency-dependent characteristic impedance, damping and wave length. The length of one of these onions is half a wave length. It is possible to read the wavelength of 23 cm that is to be expected from the diagram.

But if a piece of conductor of the length l having characteristic impedance that is different from $Z_0$ and $Z_L$ is inserted between, which transforms the load resistance $Z_L$ to a value $\tilde{Z}_L$, the field image changes considerably. To this end, it is favorable if Z1 is either larger or smaller than both of the other characteristic impedance values. This is demonstrated below in FIG. 9.

Figure 9:
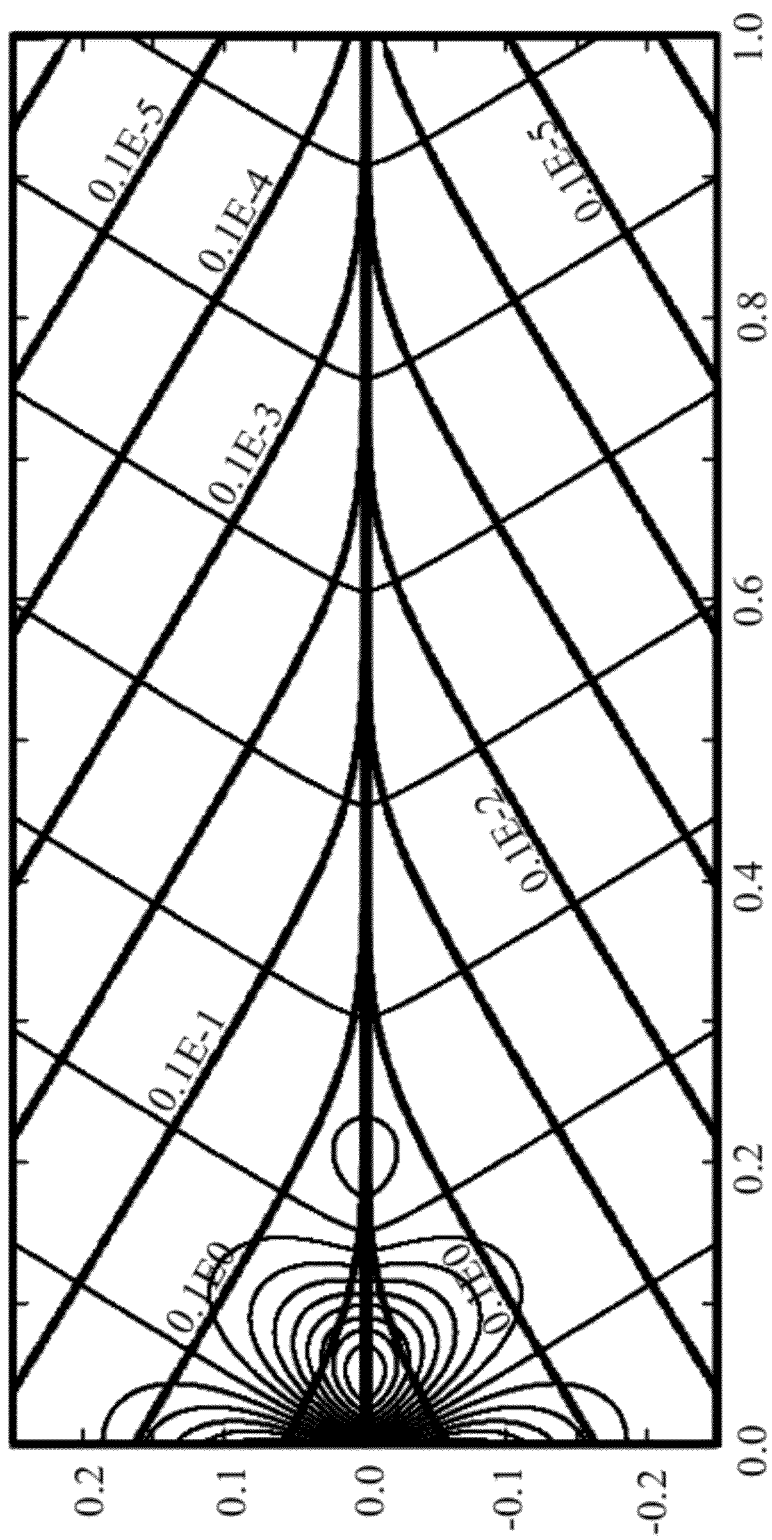

In comparison to FIG. 8, FIG. 9 shows a graphic depiction of the result of a further simulation calculation that reflects the electric field strength and the magnetic field lines and/or contour lines of magnetic flux tubes around a longitudinal section of 0 to 1 meter of a long extended electrical conductor according to the embodied example in FIG. 7. As the figure below shows, such an electrode lead also has strong damping at a frequency of 64 MHz. The energy in the right part of the diagram, which is the direction toward the distal end of the lead, is visibly lower than in the electrode lead according to the prior art, the values for which are depicted in FIG. 8.

Figure 10:
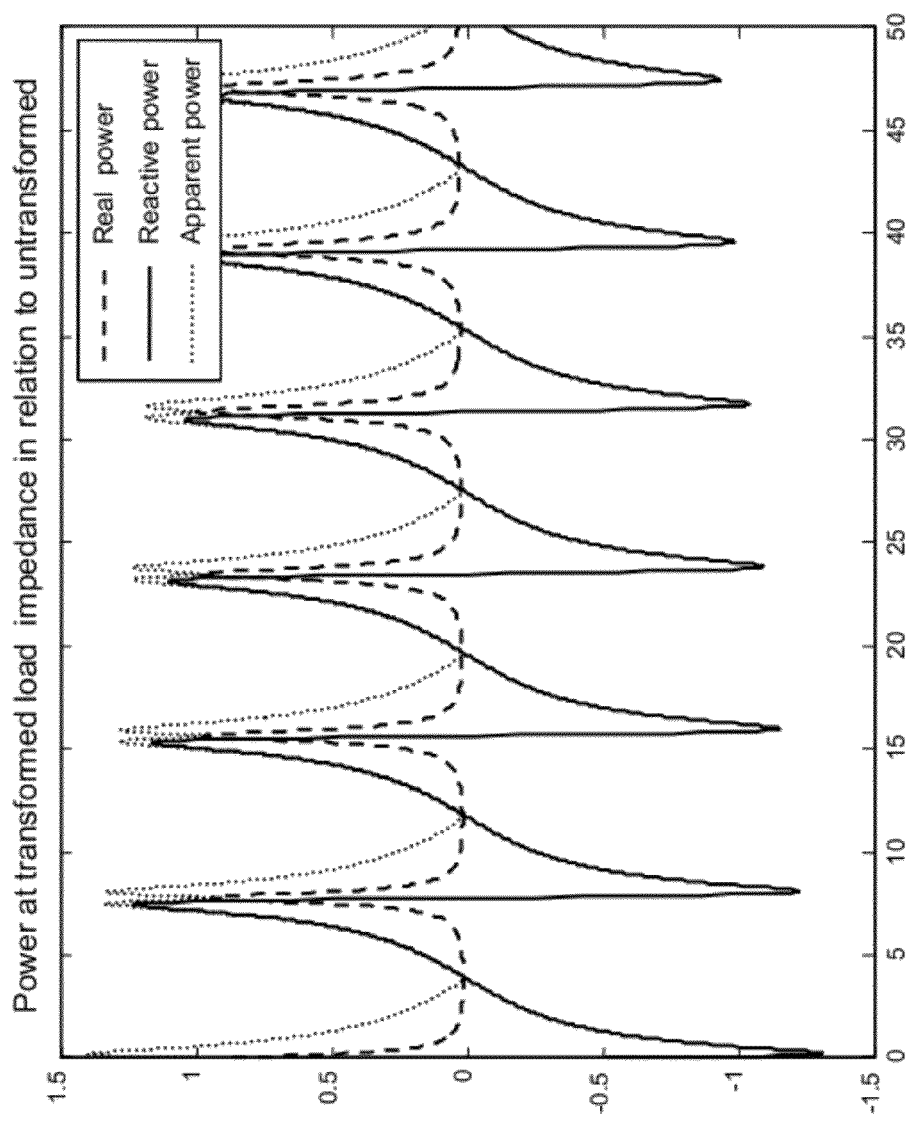
FIGS. 10 to 12 diagrams of performance parameters for an embodied example in which a weakly damped piece of a lead is inserted between an electrode pole in form of an electrode tip and the functional lead.
Figure 11:
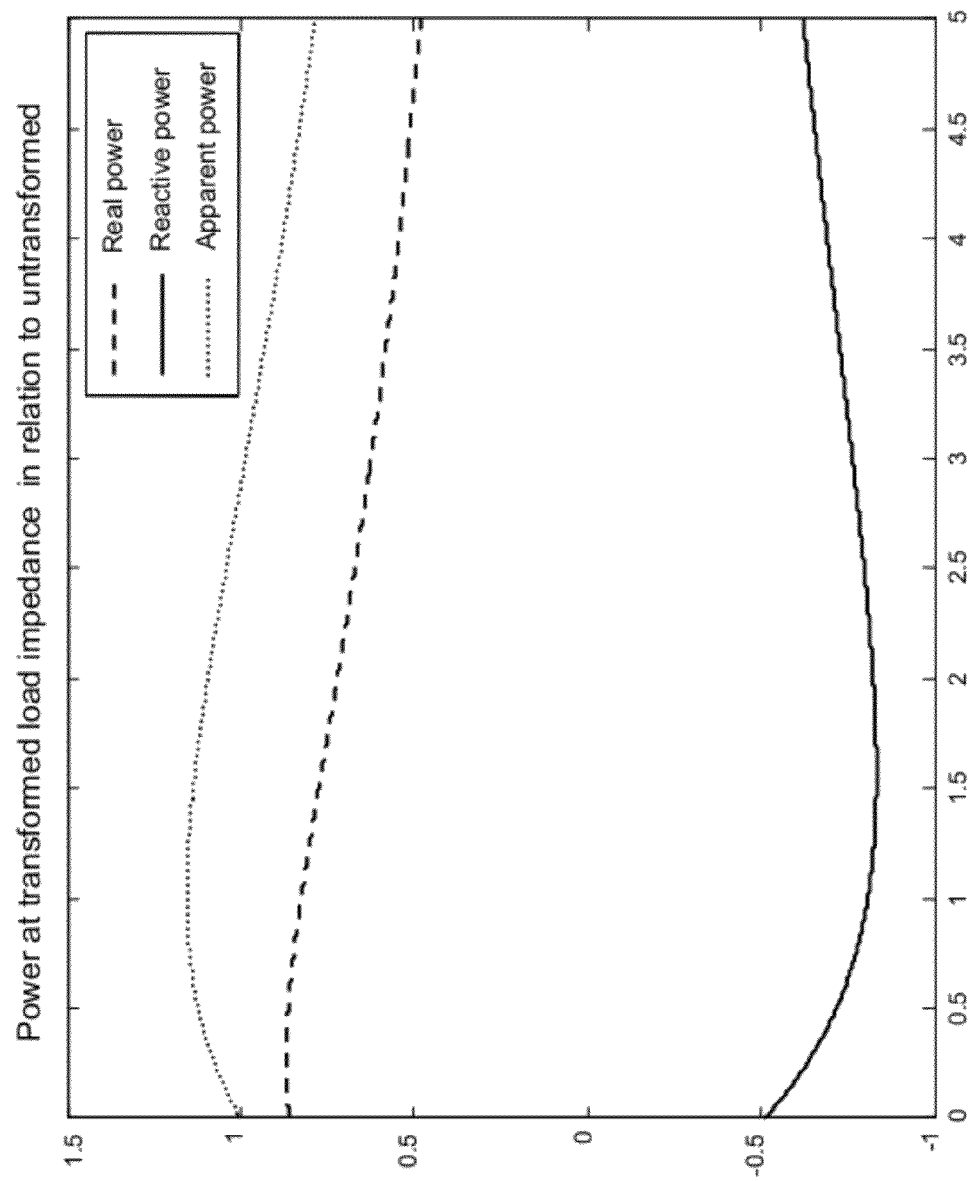
Figure 12:
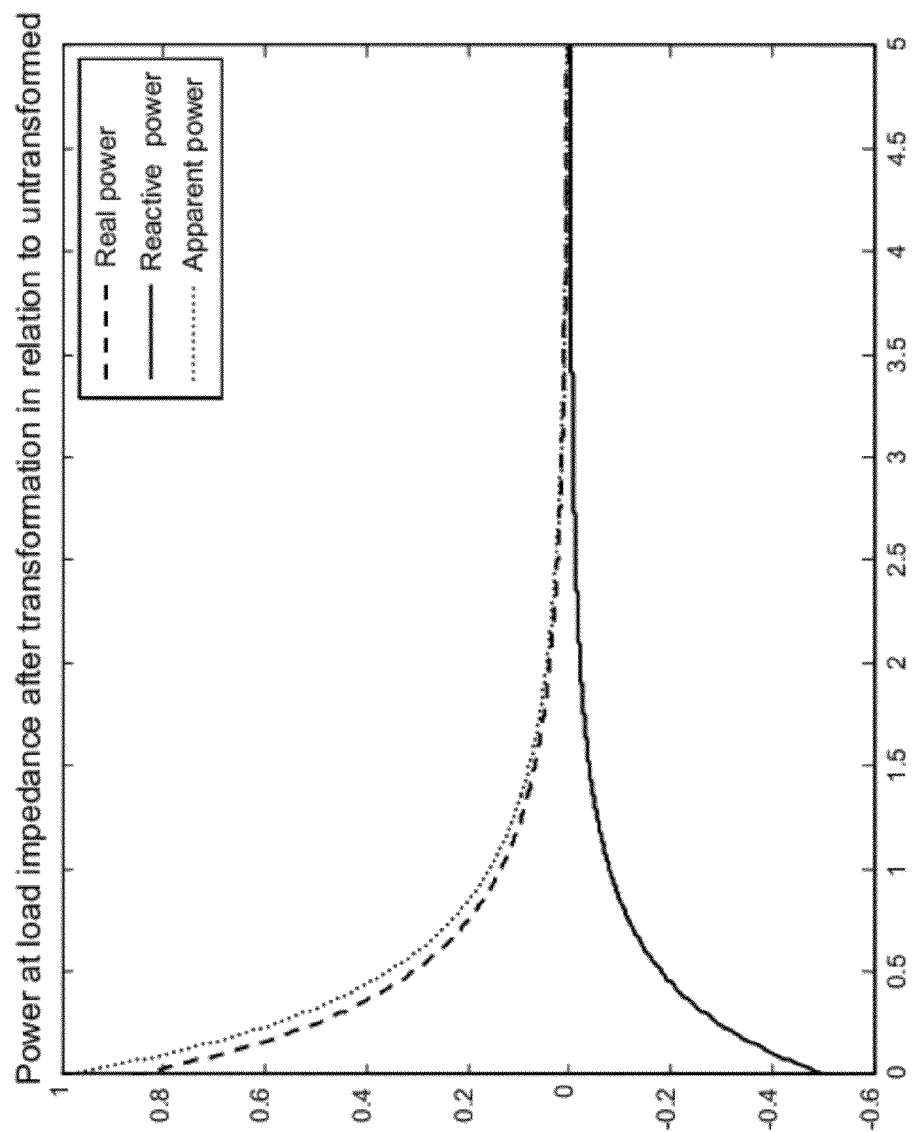

For a further illustration of the transformation properties of the power, the diagrams in FIGS. 10 to 12 first show the power at the tip of the electrode for one embodied example in which a short weakly damped piece of a lead is inserted between an electrode pole in the form of an electrode tip and a functional lead. On the abscissa of the diagrams in FIGS. 10 to 12 a length parameter is plotted in meters and on the ordinate the value of the respective performance parameter for when a piece of a lead with a length l as indicated respectively at the abscissa is interposed in relation to the respective performance parameters (l=0) without interposed piece.

FIG. 10 shows that across the length of the lead there occur periodic fluctuations of the proportions of the power parameters apparent power, reactive power and effective power. A damping is noticeable over seven periods over a length of 0 centimeter (proximal end) to 20 centimeters.

In the diagram in FIG. 11 the length of the inserted piece of a lead is plotted on the abscissa, the respective power ratio at the load resistance of the electrode tip on the ordinate. It is noticeable over the length of the almost two millimeters of ascending curves of the real power and the apparent power that the short lead piece for reducing the power parameters should be longer than two millimeters; because until a length of approximately 0.5 millimeters the ratio of real power with the additional lead piece even increases relative to the real power without the lead piece at the electrode tip due to the transformation properties. With a lead piece having a length of 1 cm, the power in the electrode tip is already reduced to one half.

The ratios look even more favorable if the damping of the lead is fully taken into account, as shown in the diagram in FIG. 12. Fully taking into account the damping, the power at the load resistance (electrode tip) drops already after 1 millimeter lead to below one half of the value from at the beginning of the lead.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising:
   a dielectric with an inside diameter $d_{iel}$;
   at least one extended electrical conductor that is insulated from surrounding material by the dielectric;
   an electrode pole coupled with said at least one extended electrical conductor and configured to emit therapy signals or configured to detect diagnostic signals that represents a load impedance $Z_L$ of electromagnetic waves when said electrode pole is in an implanted state;
   at least one first longitudinal section situated between a proximal end of said at least one extended electrical conductor and said electrical pole, wherein said at least one first longitudinal section comprises a first characteristic impedance $Z_0$ for electromagnetic waves; and,
   at least one second longitudinal section situated adjacent to the at least one first longitudinal section, wherein said at least one second longitudinal section is at least 0.25 inside diameters ($d_{iel}$) long, and is shorter than the first longitudinal section and comprises a characteristic impedance $Z_1$ for electromagnetic waves, and wherein the second characteristic impedance is larger or smaller than the first characteristic impedance $Z_0$ and larger or smaller than the load impedance $Z_L$; and,
   wherein a real part of the second characteristic impedance for electromagnetic waves is smaller by a factor of at least 2 than the real part of the first characteristic impedance.

2. The medical device as claimed in claim 1, further comprising another first longitudinal section of the first characteristic impedance $Z_0$ situated in a direction toward a distal end of said at least one extended electrical conductor after the at least one second longitudinal section.

3. The medical device as claimed in claim 1, wherein the at least one second longitudinal section is longer than 2 millimeters.

4. The medical device as claimed in claim 1, wherein the at least one second longitudinal section is shorter than 20 millimeters.

5. The medical device as claimed in claim 1, wherein the at least one second longitudinal section has a maximum length of 10 millimeters.

6. The medical device as claimed in claim 1, further comprising a functional lead that comprises a center conductor and a hollow-cylindrical outer conductor, and wherein the center conductor has a geometrical form in the second longitudinal section that differs from the geometrical form of the center conductor in the first longitudinal section.

7. The medical device as claimed in claim 6, wherein the center conductor comprises a shape of a hollow coil in the first longitudinal section of the at least one extended electrical conductor and that of the second longitudinal section is cylinder-shaped.

8. The medical device as claimed in claim 7, wherein the cylinder-shaped center conductor in the second longitudinal section is insulated by the dielectric wherein the dielectric is at least 5 micrometers thickness.

9. The medical device as claimed in claim 1, wherein the electrode pole comprises an electrode tip at a distal end of the at least one extended electrical conductor.

10. The medical device as claimed in claim 9, wherein the electrode tip is situated immediately after the second longitudinal section.

11. An implantable medical device comprising:
    a dielectric with an inside diameter $d_{iel}$;
    at least one extended electrical conductor that is insulated from surrounding material by the dielectric;

an electrode pole coupled with said at least one extended electrical conductor and configured to emit therapy signals or configured to detect diagnostic signals that represents a load impedance $Z_L$ of electromagnetic waves when said electrode pole is in an implanted state;

at least one first longitudinal section situated between a proximal end of said at least one extended electrical conductor and said electrode pole, wherein said at least one first longitudinal section comprises a first characteristic impedance $Z_0$ for electromagnetic waves;

at least one second longitudinal section situated adjacent to the at least one first longitudinal section, wherein said at least one second longitudinal section is at least 0.25 inside diameters ($d_{iel}$) long, and is shorter than the first longitudinal section and comprises a characteristic impedance $Z_1$ for electromagnetic waves, and wherein the second characteristic impedance is larger or smaller than the first characteristic impedance $Z_0$ and larger or smaller than the load impedance $Z_L$; and, a functional lead that comprises a center conductor and a hollow-cylindrical outer conductor, and wherein the center conductor has a geometrical form in the second longitudinal section that differs from the geometrical form of the center conductor in the first longitudinal section.

12. The medical device as claimed in claim 11, further comprising another first longitudinal section of the first characteristic impedance $Z_0$ situated in a direction toward a distal end of said at least one extended electrical conductor after the at least one second longitudinal section.

13. The medical device as claimed in claim 11, wherein the at least one second longitudinal section is longer than 2 millimeters.

14. The medical device as claimed in claim 11, wherein the at least one second longitudinal section is shorter than 20 millimeters.

15. The medical device as claimed in claim 11, wherein the at least one second longitudinal section has a maximum length of 10 millimeters.

16. The medical device as claimed in claim 11, wherein the center conductor comprises a shape of a hollow coil in the first longitudinal section of the at least one extended electrical conductor and that of the second longitudinal section is cylinder-shaped.

17. The medical device as claimed in claim 16, wherein the cylinder-shaped center conductor in the second longitudinal section is insulated by the dielectric wherein the dielectric is at least 5 micrometers thickness.

18. The medical device as claimed in claim 11, wherein the electrode pole comprises an electrode tip at a distal end of the at least one extended electrical conductor.

19. The medical device as claimed in claim 18, wherein the electrode tip is situated immediately after the second longitudinal section.

* * * * *